United States Patent
Serizawa (10) Patent No.: US 11,850,213 B2
(45) Date of Patent: Dec. 26, 2023

(54) OPHTHALMIC COMPOSITIONS OF RIFAMYCINS AND USES THEREOF

(71) Applicant: AMD THERAPEUTICS LLC, Middletown, DE (US)

(72) Inventor: Hiroaki Serizawa, Palo Alto, CA (US)

(73) Assignee: AMD THERAPEUTICS LLC, Middletown, DE (US)

( * ) Notice: Subject to any disclaimer, the term of this patent is extended or adjusted under 35 U.S.C. 154(b) by 170 days.

(21) Appl. No.: 17/098,272

(22) Filed: Nov. 13, 2020

(65) Prior Publication Data

US 2021/0369726 A1   Dec. 2, 2021

Related U.S. Application Data

(63) Continuation of application No. 15/327,951, filed as application No. PCT/US2015/041196 on Jul. 20, 2015, now abandoned.

(60) Provisional application No. 62/174,884, filed on Jun. 12, 2015, provisional application No. 62/136,222, filed on Mar. 20, 2015, provisional application No. 62/027,189, filed on Jul. 21, 2014.

(51) Int. Cl.
| | |
|---|---|
| A61K 31/5383 | (2006.01) |
| A61K 31/496 | (2006.01) |
| A61K 9/00 | (2006.01) |
| A61K 9/08 | (2006.01) |
| A61K 31/435 | (2006.01) |
| A61K 47/02 | (2006.01) |
| A61K 47/10 | (2017.01) |
| A61K 47/14 | (2017.01) |
| A61K 47/26 | (2006.01) |

(52) U.S. Cl.
CPC ........ *A61K 31/5383* (2013.01); *A61K 9/0048* (2013.01); *A61K 9/08* (2013.01); *A61K 31/435* (2013.01); *A61K 31/496* (2013.01); *A61K 47/02* (2013.01); *A61K 47/10* (2013.01); *A61K 47/14* (2013.01); *A61K 47/26* (2013.01)

(58) Field of Classification Search
CPC .... A61K 31/5383; A61K 9/0048; A61K 9/08; A61K 31/435; A61K 31/496
See application file for complete search history.

(56) References Cited

U.S. PATENT DOCUMENTS

| | | | |
|---|---|---|---|
| 3,342,810 A | 9/1967 | Nicola et al. | |
| 4,219,478 A | 8/1980 | Marsili et al. | |
| 4,983,602 A | 8/1991 | Yamane et al. | |

(Continued)

FOREIGN PATENT DOCUMENTS

| | | |
|---|---|---|
| CN | 1033936 A | 7/1989 |
| CN | 1511526 A | 7/2004 |

(Continued)

OTHER PUBLICATIONS

Patel et al., Der Pharmacia Lettre, 2010, 2(4): 100-115 (Year: 2010).*

(Continued)

*Primary Examiner* — San Ming R Hui
(74) *Attorney, Agent, or Firm* — Foley & Lardner LLP (57) ABSTRACT

Provided herein are ophthalmic pharmaceutical formulations comprising a rifamycin compound. Also provided herein are methods of treating ocular diseases or disorders by administering such ophthalmic formulations.

14 Claims, 2 Drawing Sheets

(56) References Cited

U.S. PATENT DOCUMENTS

| | | | |
|---|---|---|---|
| 6,218,368 | B1 | 4/2001 | Wirostko |
| 6,949,241 | B2 | 9/2005 | Molnarne-Kahan |
| 2003/0096735 | A1 | 5/2003 | D'Amato |
| 2003/0124112 | A1 | 7/2003 | Molnarne-Kahan |
| 2006/0035878 | A1 | 2/2006 | Shichiri et al. |
| 2008/0213188 | A1* | 9/2008 | Ferrari .................... A61P 27/02 424/9.1 |

FOREIGN PATENT DOCUMENTS

| | | |
|---|---|---|
| JP | 2004-075665 A | 3/2004 |
| JP | 2012-511559 A | 5/2012 |
| JP | 2013-537182 A | 9/2013 |
| WO | WO-2009/105534 | 8/2009 |
| WO | WO-2010/067072 A1 | 6/2010 |
| WO | WO-2012/035283 A1 | 3/2012 |

OTHER PUBLICATIONS

Anjo, Saeko et al., "The Effect of Non-Ionic Surfactants on the Solubility and Stability of Rifampicin," Japanese Journal of Hospital Pharmacy, vol. 13, Issue No. 5 (1987), pp. 288-292.
Bahar et al. "Anterior segment uses of bevacizumab". Current Opinion in Ophthalmology, Jul. 1, 2012, vol. 23, Issue 4, pp. 303-316.
Braha, Steriana et al., "Enhancement of Dissolution of Rifampicine and in Vitro /In Vivo Evaluation of Drug Release From Collyrium". Farmacia, 2009. vol. LVII, 1.
Cheng JW et al., "Anti-vascular endothelial growth factor for control of wound healing in glaucoma surgery". Cochrane Database of Systematic Reviews, Jan. 15, 2016, Issue 1, pp. 1-47.
Chikaraishi et al. "Rifampicin Inhibits the Retinal Neovascularization in Vitro and in Vivo". Experimental Eye Research, 2008, 86(1), pp. 131-137.
Chikaraishi et al., "Rifampicin inhibits the retinal neovascularization in vitro and in vivo". Experimental Eye Research, Oct. 14, 2007 (Oct. 14, 2007) vol. 86, pp. 131-137.
Chikaraishi, Yuichi et al., "Rifampicin Inhibits the Retinal Neovacularization in Vitro and in Vivo". Experimental Eye Research vol. 86, Issue 1, (Jan. 2008) pp. 131-137.
Darougar et al., "Topical therapy of hyperendemic trachoma with rifampicin, oxytetracycline, or spiramycin eye ointments". British Journal of Opthalmology, 1980, pp. 37-42.
Darougar et al., "Treatment of TRIC infection of the eye with rifampicin or chloramphenicol". British Journal of Ophthalmology, 1977, pp. 255-259.
Fiebai et al., "Intravitreal Anti Vascular Endothelial Growth Factor Agents in The Management of Retinal Diseases: An Audit". The Open Ophthalmology Journal, Oct. 31, 2017, vol. 11, pp. 315-321.

Genentech USA, Inc., "Lucentis Ranibizumab Injection" (2019), from https://www.lucentis.com/.
Jiao, Advanced Drug Delivery Reviews, 2008,60: 1663-1673 (Year: 2008).
Kaur, Pal et al. "Ocular Preparations: The Formulation Approach". Drug Development and Industrial Pharmacy, 28:5, pp. 473-493, 2002, DOI: 10.1081/DDC-120003445.
Khan et al., "Effect of half adult dose of oral Rifampicin (300mg) in patients with idiopathic central serous chorioretinopathy". Park J. Med. Sci., 2016, vol. 32, No. 5, pp. 1158-1163.
Kilic et al., "Rifampicin inhibits neurodegeneration in the optic nerve transaction model in vivo and after 1-methyl-4-phenylpyridinium intoxication in vitro." Acta Neuropathol, May 8, 2004 (May 8, 2004), vol. 996, pp. 65-68.
Kim, G. A. et al., "Clinical characteristics of responders to intravitreal bevacizumab in central serous chorioretinopathy patients". Eye (London, England), 2015, vol. 29,6, pp. 732-740.
Mohamed, Tarek A et al. "Effect of single subconjunctival injection of bevacizumab on primary pterygium: clinical, histopathological and immunohistochemical study". International Journal of Ophthalmology, May 18, 2018, vol. 11,5, pp. 797-801.
Nogrady, "4. Pro-Drugs and Soft Drugs", 1985, Medicinal Chemistry A Biochemical Approach, Oxford University Press, New York, pp. 388-392.
PCT International Preliminary Report on Patentability for PCT/US2015/041196 dated Feb. 2, 2017. (9 pages).
PCT International Search Report and Written Opinion for Application No. PCT/US2015/041196 dated Oct. 16, 2015. (11 pages).
Physician's Desk Reference for Ophthalmology (1982 Edition, published by Medical Economics Company, Inc., Oridell, New Jersey), wherein numerous sterile ophthalmologic ocular solutions are reported, e.g., see pp. 112-114.
Product Information for Rifabutin—Item No. 16468, Cayman Chemical Company, Sep. 22, 2014.
Remington Pharmaceutical Science, 17th Ed., 1985, p. 1553-1566 (Year: 1985).
Shichiri et al. "Rifampicin as an Oral Angiogenesis Inhibitor Targeting Hepatic Cancers". Cancer Research, Jun. 1, 2009 (Jun. 1, 2009), pp. 4760-4768.
Steinle et al., "Oral rifampin utilization for the treatment of chronic multifocal central serous retinopathy." Br J Ophthalmol, Nov. 3, 2011 (Nov. 3, 2011), vol. 96, pp. 10-13.
Yulug et al., "Rifampicin attenuates brain damages in focal ischemia". Brain Research, Jan. 16, 2014 (Jan. 16, 2004), vol. 996, pp. 76-80.
Kishi et al., "Investigation of the Stability and Effectiveness of 0.1% Rifampicin Solution in a Cold Place and at Body Temperature," Journal the Sakakibara Heart Institute of Okayama, vol. 11, pp. 78-80, 2007.

* cited by examiner

OPHTHALMIC COMPOSITIONS OF RIFAMYCINS AND USES THEREOF

REFERENCE TO RELATED APPLICATIONS

This application is a continuation of U.S. patent application Ser. No. 15/327,951, filed Jan. 20, 2017, which is a 371 National Stage Entry of International Patent Application No. PCT/US2015/041196, filed Jul. 20, 2015, which claims priority to U.S. Provisional Application Ser. No. 62/027,189 filed Jul. 21, 2014, 62/136,222 filed Mar. 20, 2015, and 62/174,884 filed Jun. 12, 2015, the content of each of which are incorporated herein in their entireties by reference.

FIELD OF THE INVENTION

Provided herein are pharmaceutically acceptable compositions or compositions suitable for topical administration to an eye, the composition comprising a therapeutically-effective amount of an antimicrobial agent, which, in a preferred embodiment comprises a rifamycin derivative, methods for their preparation, and methods for their use in treating various disorders.

BACKGROUND

Loss of visual acuity is a common problem associated with aging and with various diseases of the eye such as macular degeneration, ocular histoplasmosis syndrome, myopia, diabetic retinopathy and inflammatory diseases all of which result from neovascularization in the cornea, retina or choroid.

Age-Related Macular Degeneration (AMD) is a common eye condition which usually affects older adults and results in a loss of vision in the center of the visual field (the macula) due to retinal damage. Although some peripheral vision remains, it is difficult or impossible to read or recognize faces. There are two major forms of macular degeneration: atrophic (dry) and exudative (wet). In dry (non-exudative) form, cellular debris called drusen accumulates between retina and choroid. In more severe wet (exudative) form, blood vessels grow up from the choroid behind the retina. AMD is a leading cause of blindness among people older than 65 years and is caused by abnormal development of blood vessels behind retina. The advanced AMD population will grow by 11% to 3.3 million due to the aging population. Intravitreal injection with anti-vascular endothelial growth factor (anti-VEGF) therapy has become the criterion standard for treatment of choroidal neovascular membranes (CNVs) associated with AMD. Treatment options in wet AMD include bevacizumab (Avastin, Genentech, San Francisco, CA), which is a full-length anti-VEGF antibody, ranibizumab (Lucentis, Genentech), which is an affinity-matured fragment, pegaptanib sodium (Macugen, OSI/Eyetech Inc.), and aflibercept (Eylea, Regeneron, Tarrytown, NY), and other anti-VEGF drugs. However, intravitreal injection is a process that requires great precision, because it is performed with the help of a needle under local anesthesia. In this process, the needle must be inserted into the vitreous liquid that fills the cavity between the lens and retina, and one must be very careful not to damage the retina. Accordingly, easy treatment method for AMD is highly desirable. Therefore, a need exists for additional therapeutics and administration routes and methods for treating ocular disorders such as AMD.

SUMMARY OF THE INVENTION

This invention relates generally to pharmaceutical compositions or formulations suitable for administration to an eye. In some aspects, this invention relates to ophthalmic pharmaceutical compositions or formulations comprising one or more rifamycin compounds selected from the group consisting of rifampicin, rifabutin, rifapentine.

In one aspect, the invention relates to methods of treating an ocular disease, disorder or condition comprising administering to a patient in need thereof an ophthalmic composition comprising an effective amount of a rifamycin compound selected from the group consisting of rifampicin, rifabutin, rifapentine and rifaximin. In some aspects, this invention relates to methods for treating disorders mediated by inhibition of neovascularization in retina tissues. In other aspects, this invention relates to methods of treating age-related macular degeneration using ophthalmic compositions of rifamycin compounds. In yet other aspects, the invention related to methods for protecting retina ganglion cells and/or brain damage using ophthalmic compositions of rifamycin compounds. In further aspects, the invention relates to methods of reducing retina thickness in a patient in need thereof comprising administering to the patient an ophthalmic composition comprising an effective amount of a rifamycin compound selected from the group consisting of rifampicin, rifabutin, rifapentine and rifaximin or a pharmaceutically acceptable salt thereof.

In one aspect, provided herein is a method of inhibiting ocular neovascularization in a retina of a patient in need thereof, comprising administering topically a pharmaceutically acceptable composition comprising up to about 1% (g/100 mL of the composition weight/volume or (w/v)), or about 0.1% to about 1%, or about 0.25% to about 1%, or about 0.5% to about 1%, or about 0.1% to about 0.5%, or about 0.25% to about 0.5%, or about 0.25%, or about 0.5% of rifampicin and at least one pharmaceutically acceptable excipient to an eye of the patient containing the retina.

In other aspects, eye drop and injectable formulations of AMD101 (Rifampicin) are provided. In $H_2O$, the AMD101 can dissolve at approximately 1.4 mg/ml only. However, the concentration was increased as provided herein employing suitable excipients. Those formulations are stable for weeks.

In another aspect, provided herein is a pharmaceutically acceptable composition, preferably a topical eye drop composition comprising up to about 1% (g/100 mL of the composition weight/volume or (w/v)), or about 0.1% to about 1%, or about 0.25% to about 1%, or about 0.5% to about 1%, or about 0.1% to about 0.5%, or about 0.25% to about 0.5%, or about 0.25%, or about 0.5% of rifampicin and at least one pharmaceutically acceptable excipient.

In one aspect, provided herein is a pharmaceutically acceptable composition for subcutaneous injection comprising up to about 1% (g/100 mL of the composition weight/volume or (w/v)), or about 0.1% to about 1%, or about 0.25% to about 1%, or about 0.5% to about 1%, or about 0.1% to about 0.5%, or about 0.25% to about 0.5%, or about 0.25%, or about 0.5% of rifampicin and at least one pharmaceutically acceptable excipient.

In some embodiment, the pharmaceutically acceptable composition provided or utilized herein is at a pH of 7-8.5, 7.5-8.0, 7.5-9.0, or 7.5-12.0. In some embodiment, the pharmaceutically acceptable composition provided or utilized herein is at a pH of 2.0-7.0, 3.0-7.0, and 4.0-7.0. In some embodiment, the pharmaceutically acceptable composition provided or utilized herein are at a physiological salt concentration. In some embodiment, the pharmaceutically acceptable composition provided or utilized herein comprise one or more of an anti-oxidant, a preservative, and other pharmaceutically acceptable excipients.

The foregoing general description and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIGS. 1A-1H show histology sections of retinas treated with AMD101 topical eye drop formulation, AMD101 SC injection, and a vehicle only control, in which oxygen-induced retinopathy was induced in the retinas; and a retina in which retinopathy was not induced.

DETAILED DESCRIPTION OF THE INVENTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). The description of the preferred embodiment as set forth herein, and as depicted in the drawings, is provided for illustrative purposes only.

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

Combinations of substituents and variables are only those that result in the formation of stable compounds. The term "stable," as used herein, refers to compounds which possess stability sufficient to allow manufacture and which maintains the integrity of the compound for a sufficient period of time to be useful for the purposes detailed herein.

As used herein, "hydrate" is a form of a compound wherein water molecules are combined in a certain ratio as an integral part of the structure complex of the compound.

As used herein, "solvate" is a form of a compound where solvent molecules are combined in a certain ratio as an integral part of the structure complex of the compound.

The terms "pharmaceutically acceptable" or "pharmacologically acceptable," as used herein, refer to compositions that are generally safe, non-toxic and neither biologically nor otherwise undesirable and do not substantially produce adverse allergic or immunological reactions when administered to a host (e.g., an animal or a human). Such formulations include any pharmaceutically acceptable dosage form.

"Pharmaceutically acceptable salts" or "salts thereof" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included are pharmaceutically acceptable salts or compounds of any of the Formulae herein.

Depending on its structure, the phrase "pharmaceutically acceptable salt," as used herein, refers to a pharmaceutically acceptable organic or inorganic acid or base salt of a compound. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3 hydroxy 2 naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p toluenesulfonate, salicylate, stearate, subacetate, succinate, sulfate, sulfosalicylate, suramate, tannate, tartrate, teoclate, tosylate, triethiodide, and valerate salts.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example, in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof.

The terms "carrier" and "vehicles" as used herein, refers to relatively nontoxic chemical compounds or agents that facilitate the incorporation of a compound into cells, e.g., ocular cells, or tissues. Carriers and vehicles useful herein include any such materials known in the art, which are nontoxic and do not interact with other components of the formulation in which it is contained in a deleterious manner. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs.

The term "ophthalmically acceptable" with respect to a formulation, composition or ingredient herein means having no persistent detrimental effect on the treated eye or the functioning thereof, or on the general health of the subject being treated, baring transient effects such as minor irritation or a "stinging" sensation.

The term "active agent" or "active ingredient" is used herein to refer to a chemical material or compound that induces a desired beneficial effect when administered to a patient. Also included are salts, derivatives and analogs of those compounds or classes of compounds specifically mentioned (e.g., rifamycin compounds) that also induce the desired effect. For example, "rifampicin" as used herein includes pharmaceutically acceptable salts thereof and derivatives thereof.

The terms "buffer" or "buffering agents" refer to materials which when added to a solution, cause the solution to resist changes in pH.

The term "dilution" refers to dilution of the formulations of the present invention or those derived from the formulations of the present invention using, for example, an aqueous system comprised of physiologically balanced saline solution (PBS), such as phosphate buffered saline, or water, or other water soluble components, to the desired final concentration.

The term "subject" as used herein refers to organisms to be treated by the compositions of the present invention. Such organisms include animals (domesticated animal species, wild animals), preferably a mammal, including a human or non-human. The terms patient and subject may be used interchangeably.

The term "surfactant" refers to any molecule having both a polar head group, which energetically prefers solvation by water, and a hydrophobic tail which is not well solvated by water. Surfactants can be ionic or non-ionic. The term "ionic surfactant" includes cationic, anionic, and zwitterionic surfactants. The term "cationic surfactant" refers to a surfactant with a cationic head group. The term "anionic surfactant" refers to a surfactant with an anionic head group.

"Macular degeneration" refers to a variety of degenerative conditions characterized by central visual loss due to deterioration of the macula. One of these conditions is age related macular degeneration (AMD), which exists in both "dry" and "wet" forms.

"Ocular neovascularization" refers to the abnormal development, proliferation, and/or growth of blood vessels on or in the eye, e.g., on the retinal surface.

Methods

Some embodiments provided herein describe a method of treating visual disorders such as age-related macular degeneration (AMD), ocular neovascularization, optic neuropathy, glaucoma, degeneration of optic nerves, and ophthalmoplegia. Any ophthalmic formulation and/or compounds described above are useful in the methods described herein.

In some embodiments, a method of treating an ocular disease, disorder, injury or condition is provided, the method comprising administering to a patient in need thereof an ophthalmic composition comprising an effective amount of a rifamycin compound selected from the group consisting of rifampicin, rifabutin, rifapentine and rifaximin.

In some embodiments, the ocular disease, disorder, injury or condition is selected from the group consisting of macular degeneration, diabetic retinopathy, chronic glaucoma, retinal detachment, sickle cell retinopathy, age related macular degeneration (AMD), retinal ganglion cell injury, rubeosis iritis, inflammatory diseases, chronic uveitis, neoplasms, Fuchs' heterochromic iridocyclitis, neovascular glaucoma, corneal neovascularization, choroidal neovascularization, retinal neovascularization, retinal angiomatous proliferation, and the like.

In some embodiments, a method of treating ocular neovascularization is provided, the method comprising administering to a patient in need thereof an ophthalmic composition comprising an effective amount of a rifamycin compound selected from the group consisting of rifampicin, rifabutin, rifapentine and rifaximin. In some embodiments, the said treatment reduces or reverses the loss of visual acuity secondary to neovascularization of cornea, iris, retina or choroid. In some embodiments, ocular neovascularization includes neovascularization resulting following a combined vitrectomy and lensectomy, retinal ischemia, choroidal vascular insufficiency, choroidal thrombosis, carotid artery ischemia, neovascularization of the optic nerve, and neovascularization due to penetration of the eye or contusive ocular injury.

In some embodiments, a method of treating age-related macular degeneration (AMD) is provided, the method comprising administering to a patient in need thereof an ophthalmic composition comprising a therapeutically effective amount of a rifamycin compound selected from the group consisting of rifampicin, rifabutin, rifapentine and rifaximin. In some embodiments, the method includes treatment of dry form of AMD. In other embodiments, the method includes treatment of wet form of AMD.

In some embodiments, a method of treating retinal neovascularization is provided, the method comprising administering to a patient in need thereof an ophthalmic composition comprising a therapeutically effective amount of a rifamycin compound selected from the group consisting of rifampicin, rifabutin, rifapentine and rifaximin.

In some embodiments, a method of protecting optic nerve cells is provided, the method comprising administering to a patient in need thereof an ophthalmic composition comprising a therapeutically effective amount of a rifamycin compound selected from the group consisting of rifampicin, rifabutin, rifapentine and rifaximin. In some embodiments, the optic nerve cells are retinal ganglion cells.

In some embodiments, a method of inhibiting brain damage is provided, the method comprising administering to a patient in need thereof an ophthalmic composition comprising a therapeutically effective amount of a rifamycin compound selected from the group consisting of rifampicin, rifabutin, rifapentine and rifaximin.

In some embodiments of the methods, the rifamycin compound is rifampicin. In some embodiments, the rifamycin compound is rifabutin. In some embodiments, the rifamycin compound is rifapentine. In some embodiments, the rifamycin compound is rifaximin. In some embodiments, the ophthalmic composition further comprises at least one of a non-ionic tonicity adjusting agent, a salt, a preservative, a buffering agent, a surfactant, an anti-oxidant, a solubilizing agent and a stabilizer. In some embodiments, the composition is administered topically. In some embodiments, the composition is in the form of eye drops, a gel, lotion, cream, or an ointment, or is incorporated into a conformer, an implant, a stent, or an ophthalmic spray drug delivery device.

Compounds and pharmaceutical compositions of this invention may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, in addition to the administration of ophthalmic compositions, the method comprises oral administration of an effective amount of the active ingredient (e.g., rifamycin compound). Suitable oral formulations of the rifamycin compound selected from the group consisting of rifampicin, rifabutin, rifapentine and rifaximin are known in the art. Thus, the methods include a combination therapy whereby the active ingredient (e.g., rifamycin compound) is administered by to the patient via any suitable mode of administration, including topical, ocular, oral, subcutaneous, mucosal, intradermal, intranasal, buccal, sublingual, pulmonary or the like.

An effective amount of rifamycin compound is the amount required to produce a protective effect in vitro or in vivo. In some embodiments the effective amount in vitro is about from 0.1 nM to about 1 mM. In some embodiments the effective amount in vitro is from about 0.1 nM to about 0.5 nM or from about 0.5 nM to about 1.0 nM or from about 1.0 nM to about 5.0 nM or from about 5.0 nM to about 10 nM or from about 10 nM to about 50 nM or from about 50 nM to about 100 nM or from about 100 nM to about 500 nM or from about 500 nM to about 1 mM, In some embodiments, the effective amount for an effect in vivo is about 0.1 mg to about 100 mg, or preferably, from about 1 mg to about 50 mg, or more preferably, from about 1 mg to about 25 mg per kg/day, or from about 1 mg to about 12 mg per kg/day. In some other embodiments, the effective amount in vivo is from about 10 mg/kg/day to about 100 mg/kg/day, about 20 mg/kg/day to about 90 mg/kg/day, about 30 mg/kg/day to about 80 mg/kg/day, about 40 mg/kg/day to about 70 mg/kg/day, or about 50 mg/kg/day to about 60 mg/kg/day. In some embodiments, the effective amount in vivo is from about 1 mg/kg/day to about 5 mg/kg/day. In some embodiments, the effective amount in vivo is from about 6 mg/kg/day to about 12 mg/'kg/day. In one embodiment, the effective amount in vivo is about 3 mg/kg/day. In another embodiment, the effective amount in vivo is about 6 mg/kg/day. In another embodiment, the effective amount in vivo is about 12 mg/kg/day. In still some other embodiments, the effective amount in vivo is from about 00 mg/kg/day to about 1000 mg/kg/day.

Compositions

In one aspect, provided herein are compositions, preferably ophthalmic compositions comprising an effective amount of rifamycin compound, or a pharmaceutically acceptable salt thereof, and a pharmaceutically acceptable carrier.

The rifamycin class of antibiotics was originally isolated from cultures of *Streptomyces mediterranei*. Due to the large number of available analogues and derivatives generated synthetically, rifamycins have been widely utilized in the elimination of pathogenic bacteria that have become resistant to commonly used antibiotics.

Rifamycins are primarily effective against mycobacteria and are therefore used to treat chronic infections including tuberculosis (TB), leprosy and mycobcterium avium complex (MAC) infections. Along with its pulmonary effects, TB is also known to affect other organs including ocular tissues. Therefore, the effects of rifamycin on ocular TB and other ocular disorders have been studied. When chronic administration of rifampicin in HCV patients was monitored, it was observed that alpha fetoprotien which is the liver cancer marker was strongly inhibited. Rifampicin exhibits strong neovascularization effects whereby major neovascularization genes such as VEGF, HGF etc. are strongly inhibited.

Suitable rifamycin compounds include for example, rifampicin (rifampin), rifabutin, rifapentine, rifalazil and rifaximin, or a pharmaceutically acceptable salt thereof, or a derivative thereof. Syntheses of simple rifamycin derivatives is well known in the art, for example, the synthesis of rifampin (U.S. Pat. No. 3,342,810), rifabutin (U.S. Pat. No. 4,219,478), and rifalazil (U.S. Pat. No. 4,983,602) are known in the art and incorporated herein by reference.

In some embodiments, provided herein are compositions, preferably ophthalmic compositions or an eye drop composition comprising an effective amount of rifamycin compound, or a pharmaceutically acceptable salt thereof and an inert, non-eye irritating, non-toxic eye drop carrier. Such carriers are well known, and commonly referred to in, for example, the Physician's Desk Reference for Ophthalmology (1982 Edition, published by Medical Economics Company, Inc., Oridell, New Jersey), wherein numerous sterile ophthalmologic ocular solutions are reported, e.g., see pp. 112-114, which are incorporated by reference.

In some embodiments, the composition, including ophthalmic compositions described herein include for example, eye drops, solutions, ocular solutions such as contact lens solutions, suspensions, gels, creams and ointments intended for ophthalmic use. In some embodiments, the eye drops are administered with an eye dropper. In some embodiments, the ophthalmic composition is in the form of a topical eye drop. In one embodiment, the ophthalmic composition is a solution. In another embodiment, the ophthalmic composition is a suspension.

In some embodiments, the composition, including ophthalmic compositions are included in various drug delivery systems known in the art. For example, the composition can be included in an ocular solution used to clean, preserve, soak or immerse contact lenses. Soft contact lenses comprising a body formed of a hydrophilic gel material, such as 2-hydroxyethyl methacrylate (HEMA), and ocular solutions for cleaning or soaking them are known in the art and are commercially available. In one embodiment, the ophthalmic compositions are incorporated in an ocular solution used to soak and swell the hydrophilic gel containing lenses. The lens imbibes the solution comprising the active ingredient and slowly releases it upon insertion in the eye. Thus, therapeutically effective doses of the active ingredient, i.e. rifamycin compounds, are delivered to the patient wearing the contact lens. In one embodiment, contact lenses, after use in the eye can be soaked again in the ocular solution comprising a therapeutic level of the active ingredient to replenish the drug. In some embodiments, the active ingredient can be dispersed in to the matrix of the lens via the polymerization medium.

In some embodiments, provided herein are compositions, including ophthalmic compositions, wherein the concentration of the rifamycin compound is about 0.01 wt % to about 50 wt %, about 0.05 wt % to about 40 wt %, about 0.1 wt % to about 30 wt %, about 0.5 wt % to about 20 wt %, about 1.0 wt % to about 10 wt %, about 1.5 wt % to about 5 wt %, about 2.0 wt % to about 3.0 wt %, and ranges between any two of these values or less than any one of these values. In some embodiments, the ophthalmic compositions comprise about 50 wt %, 30 wt %, 20 wt %, 10 wt %, about 8 wt %, about 7 wt %, about 5 wt %, about 4 wt %, about 3.5 wt %, about 3 wt %, about 2.5 wt %, about 2 wt %, about 1.5 wt %, about 1 wt %, about 0.5 wt %, about 0.1 wt %, or about 0.05 wt % of the rifamycin compound.

In some embodiments, the composition, including an ophthalmic composition comprises a vehicle. Examples of suitable vehicles for the ophthalmic compositions include but are not limited to purified water and vegetable oils (e.g., olive oil, castor oil, sesame oil, etc.).

In some embodiments, the composition, including an ophthalmic composition further comprises one or more tonicity adjusting agents. In some embodiments, the tonicity adjusting agent is saline. Suitable tonicity adjusting agents are known in the art and include, but are not limited to, sodium chloride, potassium chloride, buffer salts, dextrin, glycerin, propylene glycol and mannitol.

In some embodiments, the composition, including an ophthalmic composition optionally comprises one or more surfactant. In some embodiments, non-ionic surfactants aid in dispersing the active ingredient (e.g., rifamycin compound) in suspensions and improve solution clarity. Suitable surfactants are known in the art and include, but are not limited to, sorbitan ether esters of oleic acid (e.g., polysorbate 80 or Tween 20 and 80), polyoxyethylene hydrogenated castor oil, cremophor, sodium alkylbenzene sulfonate, glycerol, lecithin, sucrose ester, polyoxyethylene-alkyl ether, polyoxyl stearate, polyoxyl 40 stearate, polymers of oxyethylated octyl phenol (tyloxapol) and polyoxyethylene polyoxypropylene glycol, or combinations thereof. In some embodiments, the ophthalmic composition comprises polysorbate 80, polyoxyethylene hydrogenated castor oil, lecithin or combinations thereof. In some embodiments, the amount of surfactant in the composition is about 0.1 to about 50 wt %, about 0.5 to about 40 wt %, about 0.1 to about 30 wt %, about 1 to about 20 wt %, about 2 to about 10 wt %. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of surfactant. In some embodiments, the ophthalmic composition comprises about 0.1 wt %-10 wt % of a surfactant selected from polysorbate 80, tween 80, tween 20, polyoxyethylene hydrogenated castor oil, and lecithin, or combinations thereof.

In some embodiments the compositions, including ophthalmic compositions may optionally comprise a stabilizer or anti-oxidant. Suitable stabilizers and anti-oxidants are known in the art and include, but not limited to, ascorbate, ascorbic acid, isoascorbic acid, glutathione sodium bisulfate, sodium metabisulfite, acetyl cysteine, 8-hydroxyquinoline, thiourea, tocopherols, EDTA, Sodium Formaldehyde Sulfoxylate Dihydrate, and combinations thereof. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of an anti-oxidant or stabilizer. In some embodiments, the ophthalmic composition comprises about 0.01 wt %-10 wt % of anti-oxidant or stabilizer.

In some embodiments the compositions, including ophthalmic compositions may optionally comprise a lubricant. Examples of suitable lubricants include, but are not limited to, glycerol, hydroxypropylmethyl cellulose, carboxy propylmethyl cellulose, sorbitol, polyvinyl pyrrolidone, polyethylene glycol, polyvinyl acetate, and combinations thereof. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of lubricant. In some embodiments, the ophthalmic composition comprises about 0.01 wt %-10 wt % of lubricant.

In some embodiments the compositions, including ophthalmic compositions may optionally comprise a deturgescent agent. Examples of suitable deturgescent agents include, but are not limited to, low or high molecular weight polysaccharide, such as dextran, dextran sulfate, polyvinyl pyrrolidone, polyethylene glycol, polyvinyl acetate, hydroxypropylmethyl cellulose, carboxymethyl cellulose, carboxypropylmethyl cellulose, dextrose, sucrose, other sugars, and combinations thereof. Any suitable molecular weight dextran or mixture thereof may be used, including dextran 40, dextran 70, and/or dextran 500. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of deturgescent agent. In some embodiments, the ophthalmic composition comprises about 0.01 wt %-10 wt % of deturgescent agent.

In some embodiments the compositions, including ophthalmic compositions may further comprise one or more viscosity imparting agents. In some embodiments, viscosity imparting agents increase the viscosity of ophthalmic solution and suspension. In some embodiments, viscosity imparting agents increase ocular contact time, thereby decreasing the drainage rate. In some embodiments, viscosity imparting agents increase mucoadhesion, ocular bioavailability and/or impart a lubricating effect. Examples of suitable viscosity imparting agents include, but are not limited to, carboxyvinyl polymer (e.g., Carbopol 934P or 974P), cellulosic polymers (e.g., carboxymethyl cellulose, hydroxypropylmethyl cellulose, hydroxyethyl cellulose or the like), polysaccharides (e.g., xanthan gum), polyvinyl pyrrolidone, polyvinyl alcohol, and combinations thereof. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of viscosity imparting agent. In some embodiments, the ophthalmic composition comprises about 0.01 wt %-10 wt % of viscosity imparting agent.

In some embodiments, the compositions, including ophthalmic compositions may include one or more phospholipid compounds. Suitable phospholipids are known in the art and include, but are not limited to, small alkyl chain phospholipids, phosphatidylcholine, egg phosphatidylcholine, soybean phosphatidylcholine, dipalmitoylphosphatidylcholine, soy phosphatidylglycerol, egg phosphatidylglycerol, distearoylphosphatidylglycerol, dimyristoylphosphatidylcholine, distearoylphosphatidylcholine, dilaurylphosphatidylcholine, 1-myristoyl-2-palmitoylphosphatidylcholine, 1-paimitoyl-2-myristoylphosphatidylcholine, 1-palmitoyl-2-stearoylphosphatidylcholine, 1-stearoyl-2-palmitoylphosphatidylcholine, dioleoylphosphatidylcholine, 1-palmitoyl-2-oleoylphosphatidylcholine, 1-oleoyl-2-palmitylphosphatidylcholine, dioleoylphosphatidylethanolamine, dilauroylphosphatidylglycerol, phosphatidylserine, phosphatidylethanolamine, phosphatidylinositol, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, phosphatidic acid, dimyristoylphosphatidic acid, dipaimitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, sphingolipids, brain sphingomyelin, dipalmitoylsphingomyelin, distearoylsphingomyelin, galactocerebroside, gangliosides, cerebrosides, phosphatidylglycerol, phosphatidic acid, lysolecithin, lysophosphatidylethanolamine, cephalin, cardiolipin, dicetylphosphate, distearoyl-phosphatidylethanolamine or combinations thereof. The phospholipid can also be a derivative or analogue of any of the above phospholipids. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of the phospholipid compound. In some embodiments, the ophthalmic composition comprises about 0.01 wt %-10 wt % % of the phospholipid compound.

In some embodiments, the composition, including ophthalmic compositions may optionally include preservatives. Examples of preservatives include, but are not limited to, midazolidinyl urea, methylparaben, propylparaben, phenoxyethanol, disodium EDTA, thimerosal, chlorobutanol sorbic acid, and combinations thereof. In some embodiments, the ophthalmic composition comprises about 0.01 wt %-20 wt %, about 0.1 wt %-15 wt %, about 0.15 wt %-10 wt %, about 0.2 wt %-5 wt %, about 0.25 wt %-3 wt %, about 0.3 wt %-2 wt %, about 0.1 wt %-20 wt %, about 1 wt %-10 wt %, about 2 wt %-10 wt %, about 2 wt %-8 wt %, about 2 wt %-5 wt %, about 5 wt %-10 wt %, about 5 wt %-20 wt % of the preservative. In some embodiments, the ophthalmic composition comprises about 0.01 wt %-10 wt % % of the preservative.

In some embodiments, the composition, including ophthalmic compositions may optionally include one or more buffering agents to maintain the pH of the composition at a range generally acceptable for eye drop compositions. In some embodiments, the compositions are buffered to a pH of about 4-8, preferably 3-7.5 or about 7. In some embodiments, the pH range is from about 6.8 to about 7.8. Examples of suitable buffering agents include, but are not limited to, citrates, phosphates, borates, bicarbonates, sodium salts, potassium including acids such as acetic, boric, citric, lactic, phosphoric and hydrochloric acids; bases such as sodium hydroxide, sodium phosphate, sodium borate, sodium citrate, sodium acetate, sodium lactate; and buffers such as citrate/dextrose, sodium bicarbonate and ammonium chloride and combinations thereof. The acids, bases and buffers are included in an amount required to maintain pH of the composition in an ophthalmically acceptable range.

The composition, including ophthalmic compositions may additionally include suitable diluents known in the art. In some embodiments, the diluent is an isotonic eye treatment carrier, buffered to a suitable pH, e.g. in the range of from about 4.0 to about 8.0, and containing effective amount of a wetting agent and an anti-bacterial agent.

The components of the composition, including ophthalmic compositions described above, if present, can be incorporated in the composition at a concentration in the range of about 0.001 wt %, about 0.01 wt %, about 0.02 wt %, about 0.05 wt %, about 0.1 wt %, about 0.5 wt %, about 1.0 wt %, about 2 wt %, about 5 wt %, about 10.0 wt %, about 15.0 wt %, about 20.0 wt %, about 30.0 wt %, about 40.0 wt %, about 50.0 wt %, about 60.0 wt %, about 70.0 wt %, about 90.0 wt %, and ranges between any two of these values or less than any one of these values.

The composition, including ophthalmic composition can be manufactured by methods known in the art. For example, the active ingredient i.e., the rifamycin compound is dissolved in purified water or saline and a surfactant is added to it and mixed. Further additives such as an isotonic agent such as sodium chloride and glycerin, buffer such as sodium phosphate or sodium borate, a pH-adjusting agent such as dilute hydrochloric acid and sodium hydroxide, preservatives such as potassium sorbate, an anti-oxidizing agent such as tocophenol, ascorbic acid etc., are optionally added to the mixture to obtain the ophthalmic composition.

The composition, including ophthalmic compositions are tested for various physicochemical, in vitro, and in vivo properties. Clarity is measured using visual and fluorescent microscopic methods. The presence of particulate matter is also determined to ensure that ophthalmic solutions are free from foreign particles. Light obscuration or microscopic methods are used for counting and or measuring the particle size. Isotonicity and pH of the composition is tested.

Drug content of the ophthalmic composition is evaluated by suitable analytical methods such as UV and HPLC. The compositions are tested also for preservative effectiveness, stability and shelf life as per standard guidelines. The composition can be further subjected to sterilization using various sterilization methods known in the art.

The compositions of the invention are tested for various physicochemical, in vitro, and in vivo properties. For example, the compositions are evaluated for inhibition of gene expression of neovascularization genes in vitro and protection of retina ganglion cells using suitable methods known in the art.

The ophthalmic compositions of the invention have high efficiency and are expected to exhibit high affinity to mucosa tissues, including eye ball. Some embodiments described herein relate to compositions which deliver a therapeutically effective amount of drug to the systemic circulation via the mucosa. In some embodiments, the compositions of the invention provide advantages over other forms of administration routes (e.g. oral, intravitreal etc.) which include but are not limited to avoiding first pass metabolism of drug(s), avoiding irritation of the GI mucosa, avoiding fluctuation in drug levels, predictable and extended duration of activity, minimizing undesirable side effects, suitability for drugs with short half-life and narrow therapeutic index, maintaining steady plasma concentrations of potent drugs, greater patient compliance due to elimination of multiple doses and dosage forms (oral and systemic), no requirement for local anaesthesia, no pain associated with injections, ease of administration, suitability for self-administration, and ease of terminating of therapy at any point in time.

In some embodiments, provided herein is an ophthalmic composition for use in the manufacture of a medicament for treatment of an ocular or visual disorder. In some embodiments, the ocular disease, disorder or condition is selected from age related macular degeneration (AMD), ocular neovascularization, retinal ganglion cell injury and brain damage.

In some embodiments, provided herein are formulations for treatment of an ocular disease, disorder or condition, comprising an selected from the group consisting of rifampicin, rifabutin, rifapentine and rifaximin, and at least one pharmaceutically acceptable carrier material. In some embodiments, the carrier material comprises an ocular/ophthalmic carrier. Suitable ocular/ophthalmic carrier materials are known in the art and include solution, gel or ointment, and the like. In some embodiments, the ocular/ophthalmic carrier is sterile aqueous solution. In some embodiments, the formulation further comprises one or more of a surfactant, an anti-bacterial agent, a pH buffering agent, an antioxidant agent, a preservative agent, or a combination thereof.

In some embodiments, provided herein is a composition, including an ophthalmic composition for treating age-related macular degeneration, said composition comprising an effective amount of a rifamycin compound selected from the group consisting of rifampicin, rifabutin, rifapentine and rifaximin.

In some embodiments, provided herein is a composition, including an ophthalmic composition for treating retinal neovascularization, said composition comprising an effective amount of a rifamycin compound selected from the group consisting of rifampicin, rifabutin, rifapentine and rifaximin.

In some embodiments, provided herein is a composition, including an ophthalmic composition for protecting optic nerve cells, said composition comprising an effective amount of a rifamycin compound selected from the group consisting of rifampicin, rifabutin, rifapentine and rifaximin.

In some embodiments, provided herein is a composition, including an ophthalmic composition for inhibiting brain damage, said composition comprising an effective amount of a rifamycin compound selected from the group consisting of rifampicin, rifabutin, rifapentine and rifaximin.

In another embodiment, provided herein is a composition, including a stabilized ophthalmic composition comprising rifamycin compounds wherein the composition is stable for more than three months, preferably more than six months, more preferably more than twelve months.

EXAMPLES

Example 1: Eye Drop Formulation of Rifamycin Compounds

The active ingredient, i.e. rifamipicin, rifabutin, rifapentine, rifalazil or rifaximin is dissolved in saline or water and a surfactant such as polysorbate 80, tween 80 or tween 20 is added and mixed. Further, various additives such as glycerin, xanthan gum, hydroxypropylmethylcellulose (HPMC), cyclodextrin derivatives such as hydroxypropyl-β-cyclodextrin, isotonic agents such as such as sodium chloride, potassium chloride or sodium bisulfate, preservative such as disodium EDTA or methylparaben, anti-oxidant such as ascorbic acid are optionally added and mixed to form a clear solution. The solution is optionally filtered to remove particulate matter and the pH is adjusted by adding an acid such as hydrochloric acid or a base such as sodium chloride to obtain the desired pH.

Example 2

16 different formulations were prepared for topical eye drop application of rifampicin, as disclosed in Tables 1-3. The formulations of Example 1A and Example 6A were used in the following studies.

The following eye drop formulations were prepared at room temperature (Tables 1 and 2), and Rifampicin was added to the eye drop formulations to the final concentrations listed:

TABLE 1

|  | Example 1A | Example 2A | Example 3A | Example 4A | Example 5A |
|---|---|---|---|---|---|
| pH of input buffer (50 mM Boric Acid-Borax) |  |  |  | pH 8.7 | pH 8.7 |
| pH of input buffer (100 mM Boric Acid-NaOH) | pH 8.3 | pH 8.3 | pH 8.3 |  |  |
| Final concentrations of input buffers | 10 mM | 10 mM | 20 mM | 25 mM | 25 mM |
| Final pH detected after addition of Rifampicin | pH 7.64 |  | pH 7.37 | pH 8.01 | pH 8.30 |
| NaCl* | 150 mM | 150 mM | 0.9% | 0.9% | 0.9% |
| Tween 80* | 0.5% | 0.5% | 0.5% | 0.5% | 0.5% |
| EDTA* | 0.1% | 0.1% | 0.1% | 0.1% | 0.1% |
| Benzalkonium chloride* | 0.01% | 0.01% | 0.01% | 0.01% | 0.01% |
| Rifampicin* | 0.25% | 0.5% | 0.5% | 1% | 0.5% |

*Final concentrations

TABLE 2

|  | Example 6A | Example 7A | Example 8A | Example 9A | Example 10A |
|---|---|---|---|---|---|
| pH of input buffer (50 mM Boric Acid-Borax) | pH 8.7 | pH 8.7 | pH 8.5 | pH 8.5 | pH 8.3 |
| Final concentrations of input buffers | 18 mM | 14 mM | 25 mM | 18 mM | 25 mM |
| Final pH detected after addition of Rifampicin | pH 8.01 | pH 8.02 | pH 7.81 | pH 7.69 | pH 7.47 |
| NaCl* | 0.9% | 0.9% | 0.9% | 0.9% | 0.9% |
| Tween 80* | 0.5% | 0.5% | 0.5% | 0.5% | 0.5% |
| EDTA* | 0.1% | 0.1% | 0.1% | 0.1% | 0.1% |
| Benzalkonium chloride* | 0.01% | 0.01% | 0.01% | 0.01% | 0.01% |
| Rifampicin* | 0.5% | 0.5% | 0.5% | 0.5% | 0.5% |

*Final concentrations*

Rifampicin was completely dissolved at room temperature in the eye drop formulations of Example 1A and Examples 5A-8A listed in Tables 1 and 2, and rifampicin was not precipitated in these formulations for weeks. Rifampicin solutions were stored at room temperature or in a refrigerator.

Input buffers that were added in Example 1A-10A were 50 mM Bric acid-Borax or 100 mM Boric acid-NaOH, and pH values of these input buffers were listed in Tables 1 and 2. Liquid formulations were prepared by mixing components listed in the tables, and powder of rifampicin was added and mixed in the formulations for 2-3 hr. After mixing rifampicin in the formulations, values of pH were measured, and these pH values were listed in the tables.

TABLE 3

|  | Example 11A | Example 12A | Example 13A | Example 14A | Example 15A | Example 16A |
|---|---|---|---|---|---|---|
| pH of input buffers (50 mM Boric Acid-Borax) |  |  |  |  | pH 8.7 | pH 8.7 |
| pH of input buffer (100 mM Boric Acid-NaOH) | pH 8.3 | pH 8.3 | pH 8.3 | pH 8.3 |  |  |
| Final concentrations of input buffers | 10 mM | 10 mM | 10 mM | 10 mM | 18 mM | 18 mM |

TABLE 3-continued

|  | Example 11A | Example 12A | Example 13A | Example 14A | Example 15A | Example 16A |
|---|---|---|---|---|---|---|
| Final pH after addition of all components, including rifampicin | pH 8.03 | pH 8.10 | pH 4.07 | pH 3.32 | pH 5.23 | pH 3.67 |
| NaCl* | 150 mM | 150 mM | 150 mM | 150 mM | 0.90% | 0.90% |
| Tween 80* | 0.5% | 0.5% | 0.5% | 0.5% | 0.5% | 0.5% |
| EDTA* | 0.1% | 0.1% | 0.1% | 0.1% | 0.1% | 0.1% |
| Benzalkonium chloride* | 0.01% | 0.01% | 0.01% | 0.01% | 0.01% | 0.01% |
| Rifampicin* | 2.5 mg/ml | 2.5 mg/ml | 2.5 mg/ml | 2.5 mg/ml | 5 mg/ml | 5 mg/ml |
| Sodium formaldehyde sulfoxylete dyhydrate* | 0.04 mg/ml | 0.21 mg/ml |  |  |  |  |
| L-ascorbic acid* |  |  | 0.25% | 1% | 0.25% | 1% |

*Final concentrations

Buffers, NaCl, Tween80, and EDTA that are listed in Table 3 were mixed in a beaker at room temperature, and rifampicin was added and completely dissolved in these liquid formulations at room temperature. Stock solutions of sodium formaldehyde sulfoxylete dihydrate or L-ascorbic acid were added in the formulations, and then values of pH in the formulations were measured (Examples 11A-16A). The formulations of Example 11A and 12A were stable at room temperature for more than several days, and they did not produce any precipitate. The formulations of Example 13A-16A were stable in a refrigerator for more than several days, and they did not produce any precipitate.

Example 3

Rifampicin was delivered to retina by topical eye drop application. 0.25% rifampicin eye drop formulation was used for the studies. It showed good delivery efficiency, and retina tissue got micro gram concentrations of rifampicin per g of tissue by the eye drop application.

Four male Sprague-Dawley rats (250-300 g) were used to determine retina exposure levels of rifampicin following applications of eye drops. Two rats received 3 drops of an eye drop formulation (0.25% Rifampicin) which is presented as Example 1A listed in Table 1 in each eye under isoflurane sedation. The remaining two rats received the same applications, but 10 drops, to each eye under isoflurane sedation. A single drop contained 5 micro L of the formulation, and applications of each drop had 30 min interval. After the eye drop application, retinas were extracted under a dissection microscope. In addition, "Non-treatment" negative control was taken, and retina was extracted from two rats without any treatment. Retinas were placed in a 1.5 ml microcentrifuge tubes (1 retina/tube), and they were extensively washed by DPBS. After the washing procedure, retina tissue in a microcentrifuge tube was frozen in dry ice, and it was stored for quantification by LC/MS analysis. Table 4 shows quantifications of rifampicin which was extracted from the retina tissues. Rifampicin was delivered to retina by the eye drop formulation (0.25% rifampicin) with dose dependent manner.

TABLE 4

Amounts of Rifampicin which was delivered to retina by topical eye drop application (0.25% Rifampicin)

|  | Non-Treatment | 3 drops | 10 drops |
|---|---|---|---|
| Rifampicin extracted from retinas (average of n = 3, ng/g tissue) | BDL | 1,288* | 2,939* |
| SE | N/A | 394 | 50.54 |

| Compound (Brand name) MOA for indication or usage | Drug amount dosed | Drug amount detected in retina | Ref. |
|---|---|---|---|
| Betoptic 0.5% (MW 307) betal receptor blocker for Glaucoma | 0.5% 4 drops (120-200 microL, 600-1,000 micro g) | ~300 ng/g retina tissue (Rabbit) | Osborne et al (1999) |
| Betoptic 0.5% (MW 307) betal receptor blocker for Glaucoma | 0.5% 8 drops (240-400 microL, 1200-2000 micro g) | ~480 ng/g retina tissue (Rabbit) | Osborne et al (1999) |
| Dexamethasone (MW 392) Glucocorticoid for inflammation | 0.5% 50 microL, 250 micro g | ~33 ng/g retina tissue (Rabbit) | Sigurdsson et al (2007) |
| AMD101 | 0.25%, 3 drops (15 microL, 37.5 micro g) | ~1,288 ng/g retina tissue (Rat) | This study |
| AMD101 | 0.25%, 10 drops (50 microL, 125 micro g) | ~2,939 ng/g retina tissue (Rat) | This study |

BDL: Blow Detection Limit
*Evaluated at p value of 0.014
Efficacy of retinal delivery of AMD101 by eye drop formulation >X100 of Dexamethasone retina delivery.

Example 4

This example provides experimental procedures and results of PK studies that showed rifampicin was delivered to retina by subcutaneous (SC) injection. Amounts detected by SC and by topical eye drop were equivalent.

Six male Sprague-Dawley rats (250-300 g) were used to determine retina exposure levels of rifampicin following subcutaneous injection (20 mg/Kg). A formulation which is presented as Example 6A listed in Table 2 was used to dose Rifampicin by the SC injection in this study. At time points of 1 hr, 3 hr, and 7 hr after the SC injection, retina tissues were extracted from the rats under a dissection microscope. In addition, "Non-treatment" negative control was taken, and retina was extracted from two rats without any treatment. Retinas were placed in a 1.5 ml microcentrifuge tubes (1 retina/tube), and they were extensively washed by DPBS. After the washing procedure, retina tissue in a microcentrifuge tube was frozen in dry ice, and it was stored for quantification by LC/MS analysis. Table 5 shows quantifications of rifampicin which was extracted from the retina tissues. Amounts detected in retina by the SC injection were equivalent to those delivered by the eye drop application (See Table 3).

TABLE 5

Amounts of Rifampicin which was delivered to retina by subcutaneous injection (20 mg/Kg)

| | Non-treatment | 1 hr | 3 hr | 7 hr |
|---|---|---|---|---|
| Rifampicin extracted from retinas (average of n = 4, ng/g tissue) | BDL | 2,655 | 3,864 | 2,516 |
| SE | N/A | 348 | 402 | 447 |

BDL: Blow Detection Limit

Example 5

Experimental procedures and results of PK studies using 0.25% rifampicin eye drop formulation were provided.

Six male Sprague-Dawley rats (250-300 g) were used to determine retina exposure levels of rifampicin following topical eye drop application. 15 microL of an eye drop formulation which is presented as Example 1A listed in Table 1 was used to dose the compound to a single eye of a rat. 15 micro L of the formulation contained 37.5 micro gram of rifampicin. At time points of 1 hr, 3 hr, and 7 hr after the eye drop application, retina tissues were extracted from the rats under a dissection microscope. In addition, "Non-treatment" negative control was taken, and retina was extracted from a single rat without any treatment. Retinas were placed in a 1.5 ml microcentrifuge tubes (1 retina/tube), and they were extensively washed by DPBS. After the washing procedure, retina tissue in a microcentrifuge tube was frozen in dry ice, and it was stored for quantification by LC/MS analysis. Table 6 shows quantifications of rifampicin which was extracted from the retina tissues. Rifampicin was delivered to retina by the eye drop formulation (0.25% rifampicin).

TABLE 6

Amounts of Rifampicin which was delivered to retina by topical eye drop application (0.25% Rifampicin)

| | Non-treatment | 1 hr | 3 hr | 7 hr |
|---|---|---|---|---|
| Rifampicin extracted from retinas (average of n = 4, ng/g tissue) | BDL | 1,576 | 1,151 | 104 |
| SE | N/A | 868 | 538 | 16 |

BDL: Below Detection Limit
Tmax: ~1 hr,
T½: ~3-4 hr

Example 6

Experimental procedures and results of dose-response studies using 0.25% and 0.5% rifampicin eye drop formulation were provided.

Four male Sprague-Dawley rats (250-300 g) were used to determine retina exposure levels of rifampicin following topical eye drop application. 15 microL of eye drop formulations which are presented as Example 1A and 6A listed in Table 1 and Table 2, respectively, were used to dose the compound to a single eye of a rat. 15 micro L of the formulations contained 37.5 and 75 micro gram of rifampicin, respectively. In 1 hr after the eye drop application, retina tissues were extracted from the rats under a dissection microscope. In addition, "Non-treatment" negative control was taken, and retina was extracted from a single rat without any treatment. Retinas were placed in a 1.5 ml microcentrifuge tubes (1 retina/tube), and they were extensively washed by DPBS. After the washing procedure, retina tissue in a microcentrifuge tube was frozen in dry ice, and it was stored for quantification by LC/MS analysis. Table 7 shows quantifications of rifampicin which was extracted from the retina tissues. Rifampicin was delivered to retina by both eye drop formulations with dose-response manner (0.25% and 0.5% rifampicin).

TABLE 7

Amounts of Rifampicin which was delivered to retina by topical eye drop application (0.25% and 0.5% Rifampicin)

| | Non-treatment | 0.25% Rifampicin 15 microL | 0.5% Rifampicin 15 microL |
|---|---|---|---|
| Rifampicin extracted from retinas (average of n = 4, ng/g tissue) | BDL | 1,576 | 6,068 |
| SE | N/A | 868 | 2,634 |

BDL: Below Detection Limit

Example 7

Experimental procedures of pre-clinical efficacy studies in Oxygen-Induced Retinopathy rat model using 0.25% rifampicin eye drop formulation were provided.

The Oxygen-Induced Retinopathy rat model was produced according to the protocol of Yanni et al (2010) and Dorfmann et al (2008). Sprague-Dawley rat pups (and their nursing mothers) were exposed to a cycling oxygen environment (80% and 21%, ~one day each) for 15 days starting from the day of birth (Day 0). On Day 15 (P15), the animals were moved to room air. 6 pups, 7 pups, and 6 pups were assigned to dosing groups of vehicle only control, AMD101

Figure 1A:
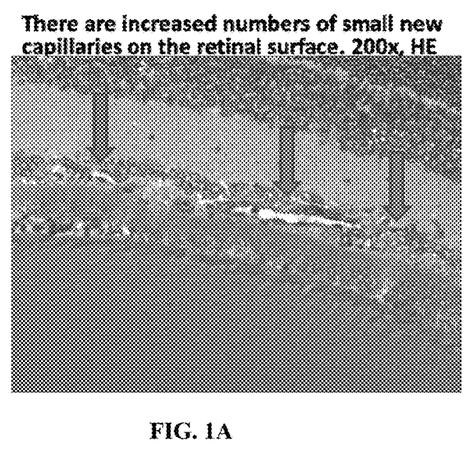
FIG. 1A shows the 200× histological section of a retina treated with a vehicle only control.
Figure 1B:
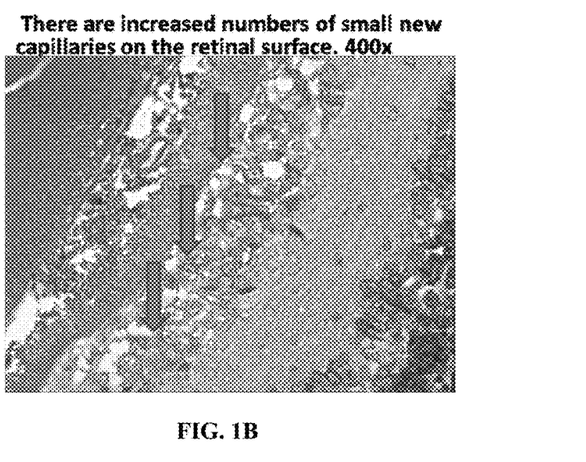
FIG. 1B shows the 400× histological section of a retina treated with a vehicle only control.
Figure 1C:
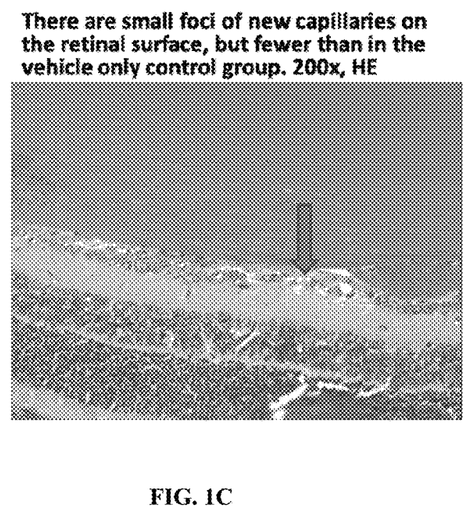
FIG. 1C shows the 200× histological section of a retina treated with AMD101 topical eye drop formulation.
Figure 1D:
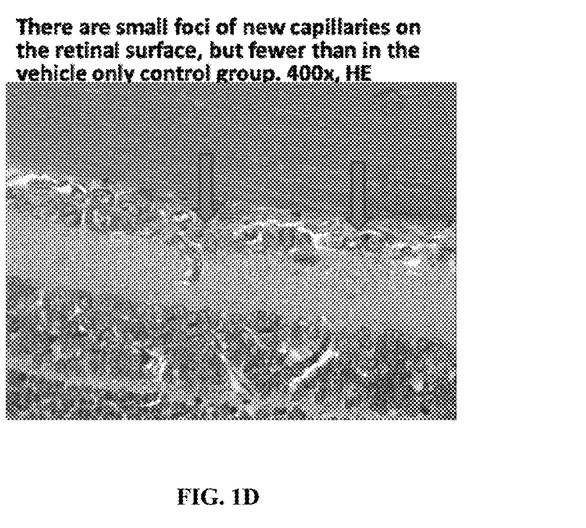
FIG. 1D shows the 400× histological section of a retina treated with AMD101 topical eye drop formulation.
Figure 1E:
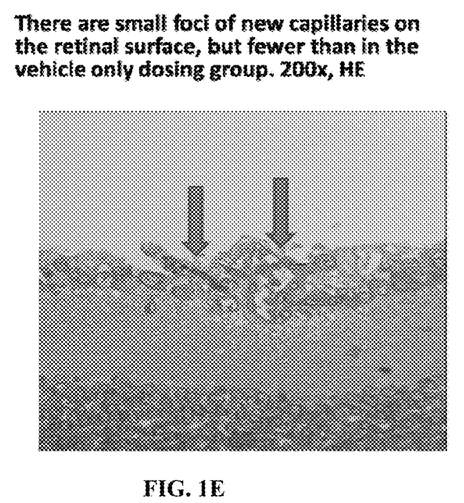
FIG. 1E shows the 200× histological section of a retina treated with AMD101 SC injection.
Figure 1F:
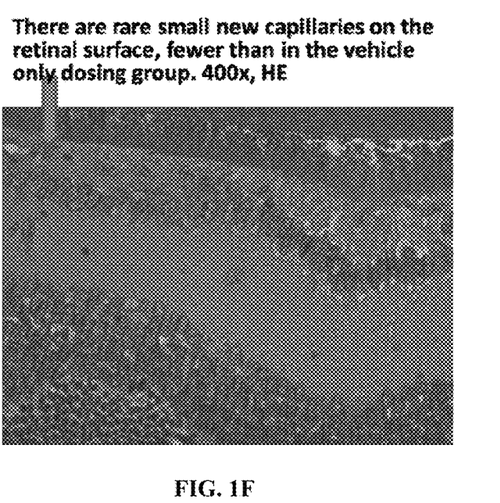
FIG. 1F shows the 400× histological section of a retina treated with AMD101 SC injection.
Figure 1G:
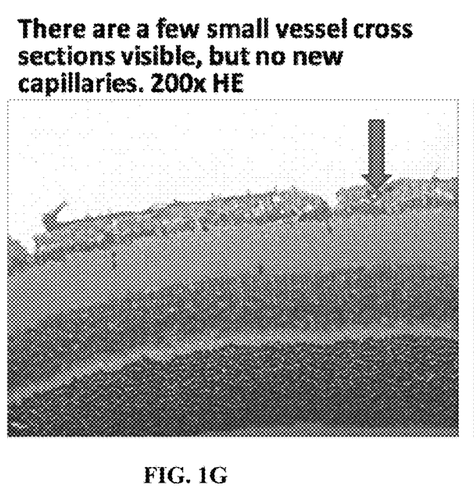
FIG. 1G shows the 200× histological section of a retina for which retinopathy was not induced.
Figure 1H:
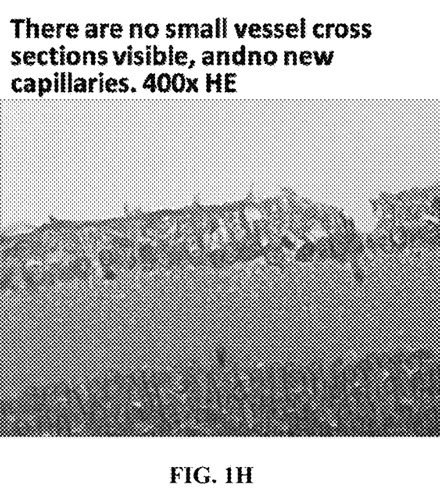
FIG. 1H shows the 400× histological section of a retina for which retinopathy was not induced.

(Rifampicin) eye drop formulation, and SC injection, respectively. An eye drop formulation which is presented as Example 1A listed in Table 1 or vehicle only was daily administered to eyes of pups for 5 days between P15 and P19 in the morning, about noon, and in the evening. A formulation which is presented as Example 6A listed in Table 2 was used to dose AMD101 (Rifampicin) to pups by the SC injection at 20 mg/Kg once daily from P15 to P19. At P20, all animals were euthanized, the retinas were visualized in histology sections. In those histology sections, neovascularization were quantified by counting capillaries in retina tissue in 3 eye balls (the dosing groups of AMD101 topical application, AMD101 SC injection, and non-induction of retinopathy) or 5 eye balls (the dosing group of vehicle only control). These eye balls were selected from different animals in the dosing groups. Representative images of the histology sections are presented (see FIGS. 1A-H). The retina treated with the vehicle only control showed increased numbers of small new capillaries on the retinal surface (see FIGS. 1A and 1B). The retina treated with the AMD101 topical eye drop formulation showed small foci of new capillaries on the retinal surface but fewer than in the control group (see FIGS. 1C and 1D). The retina treated with the AMD101 SC injection showed small foci of new capillaries on the retinal surface but fewer than in the control group (see FIGS. 1E and 1F). The retina for which retinopathy was not induced showed a few small vessel cross sections but did not show any new capillaries (see FIGS. 1G and 1H). Table 8 shows quantifications of detected capillaries in the histology sections.

TABLE 8

Neovascularization in retina in Oxygen-Induced Retinopathy rat model was quantified by detecting capillaries in histology sections

|  | Non-induction of retinopathy (n = 3) | Vehicle only control (n = 5) | 0.25% AMD101 topical eye-drop (n = 3) | 0.5% AMD101 SC injection (n = 3) |
|---|---|---|---|---|
| Average numbers of capillaries in high power field per eye | 3.33 | 16.3 | 7.78 | 9.28 |
| SE | 1.109721353 | 1.338468851 | 1.348295678 | 0.895463216 |

Vehicle only vs 0.25% AMD101 eye-drop: P-value = 0.0058
Vehicle only vs 0.5% AMD101 SC: P-value = 0.0102

Example 8

Delivery of ophthalmic formulation of rifamycin compounds via a device such as a contact lens.

The ophthalmic formulation comprising the active ingredient, i.e. rifamipicin, rifabutin, rifapentine, rifalazil or rifaximin, and a pharmaceutically acceptable carrier and optionally additives as disclosed herein are incorporated in to ocular solutions used to soak or wash the contact lenses. A hydrophilic gel based contact lens is optionally dried at ambient temperature and then dipped, washed or immersed in a solution of a soaking agent or swelling agent containing an effective amount of the ophthalmic formulation.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A method of treating an ocular disease, disorder or condition which results from ocular neovascularization comprising topically administering to a patient in need thereof a stable ophthalmic composition comprising about 0.01 wt % to 10 wt % of a solubilized rifamycin compound selected from rifampicin, rifabutin, rifapentine, rifaximin, or a pharmaceutically acceptable salt thereof, about 0.1 wt % to 50 wt % of a non-ionic surfactant, and a pH of about 2 to 12, wherein the composition does not comprise 0.1 wt % rifampicin in combination with 2 wt % polysorbate 80 (Tween 80)
    wherein the pH is buffered with a citrate, a phosphate, a bicarbonate, a sodium salt, potassium, acetic acid, citric acid, lactic acid, phosphoric acid, hydrochloric acid, sodium hydroxide, sodium phosphate, sodium citrate, sodium acetate, sodium lactate, citrate/dextrose, sodium bicarbonate, ammonium chloride, or a combination thereof, wherein the composition is stable for at least one day.

2. The method of claim 1, wherein the ocular neovascularization comprises retinal or choroidal neovascularization.

3. The method of claim 1, wherein the non-ionic surfactant is selected from the group consisting of sorbitan ether esters of oleic acid, polyoxyethylene hydrogenated castor oil, cremophor, sodium alkylbenzene sulfonate, glycerol, lecithin, sucrose ester, polyoxyethylene-alkyl ether, polyoxyl stearate, polyoxyl 40 stearate, polymers of oxyethylated octyl phenol (tyloxapol) and polyoxyethylene polyoxypropylene glycol, and a combination of two or more thereof.

4. The method of claim 1, wherein the ophthalmic composition is a topical eye drop.

5. The method of claim 1, wherein the ophthalmic composition further comprises a pharmaceutically acceptable carrier.

6. The method of claim 5, wherein the pharmaceutically acceptable carrier comprises a tonicity adjusting agent.

7. The method of claim 6, wherein the tonicity adjusting agent is selected from the group consisting of saline, dextrose, glycerin, aqueous potassium chloride, buffer salts, propylene glycol, and mannitol.

8. A method of treating an ocular disease, disorder or condition which results from ocular neovascularization comprising topically administering to a patient in need thereof a stable ophthalmic composition comprising about 0.01 wt % to 10 wt % of a solubilized rifamycin compound selected from rifampicin, rifabutin, rifapentine, rifaximin, or a pharmaceutically acceptable salt thereof, about 0.1 wt % to 50 wt % of a non-ionic surfactant, and a pH of about 2 to 12, wherein the composition does not comprise 0.1 wt % rifampicin in combination with 2 wt % polysorbate 80 (Tween 80)

wherein the pH is buffered with a borate, and wherein the composition is stable for at least one day.

9. The method of claim 8, wherein the ocular neovascularization comprises retinal or choroidal neovascularization.

10. The method of claim 8, wherein the non-ionic surfactant is selected from the group consisting of sorbitan ether esters of oleic acid, polyoxyethylene hydrogenated castor oil, cremophor, sodium alkylbenzene sulfonate, glycerol, lecithin, sucrose ester, polyoxyethylene-alkyl ether, polyoxyl stearate, polyoxyl 40 stearate, polymers of oxyethylated octyl phenol (tyloxapol) and polyoxyethylene polyoxypropylene glycol, and a combination of two or more thereof.

11. The method of claim 8 wherein the ophthalmic composition is a topical eye drop.

12. The method of claim 8, wherein the ophthalmic composition further comprises a pharmaceutically acceptable carrier.

13. The method of claim 12, wherein the pharmaceutically acceptable carrier comprises a tonicity adjusting agent.

14. The method of claim 13, wherein the tonicity adjusting agent is selected from the group consisting of saline, dextrose, glycerin, aqueous potassium chloride, buffer salts, propylene glycol, and mannitol.

* * * * *

UNITED STATES PATENT AND TRADEMARK OFFICE
CERTIFICATE OF CORRECTION

| | | |
|---|---|---|
| PATENT NO. | : 11,850,213 B2 | Page 1 of 1 |
| APPLICATION NO. | : 17/098272 | |
| DATED | : December 26, 2023 | |
| INVENTOR(S) | : Serizawa | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 206 days.

Signed and Sealed this
First Day of July, 2025

Coke Morgan Stewart
*Acting Director of the United States Patent and Trademark Office*